United States Patent

Swaminathan et al.

[11] Patent Number: 5,627,301
[45] Date of Patent: May 6, 1997

[54] PROCESS FOR THE PREPARATION OF MONO-ALKYLCARBONATE OF BISPHENOLS

[75] Inventors: Sivaram Swaminathan; Abbas A. G. Shaikh, both of Maharashtra, India

[73] Assignee: Council of Scientific & Industrial Research, New Delhi, India

[21] Appl. No.: 219,497

[22] Filed: Mar. 29, 1994

[51] Int. Cl.$^6$ ............................................. C07C 68/06
[52] U.S. Cl. ............................................. 558/270
[58] Field of Search ................................. 558/270

[56] References Cited

U.S. PATENT DOCUMENTS

| | | | |
|---|---|---|---|
| 4,217,438 | 8/1980 | Brunelle et al. | 528/202 |
| 4,349,486 | 9/1982 | Brunelle et al. | 558/274 |
| 4,973,728 | 11/1990 | Tuinstra et al. | 558/270 X |
| 5,034,557 | 7/1991 | Kiso et al. | 558/270 |
| 5,149,856 | 9/1992 | Schön et al. | 558/270 |
| 5,380,908 | 1/1995 | Murata et al. | 558/270 |

FOREIGN PATENT DOCUMENTS 0000879  3/1979  European Pat. Off..

OTHER PUBLICATIONS

Buysch, H.J. et al., Derwent Abstract No. 79–16135B; 1979; German Patent Application No. 2736062.

*Primary Examiner*—Johann Richter
*Assistant Examiner*—Michael G. Ambrose
*Attorney, Agent, or Firm*—Ladas & Parry

[57] ABSTRACT

A process for the preparation of mono-alkylcarbonate of bisphenols of the formula

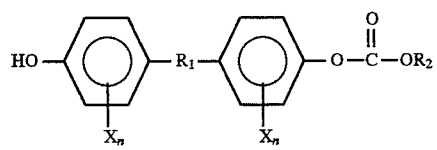

wherein $R_1$ represents ispropylidene, hexafluoroisopropylidene, cyclohexane, sulphone, ketone, ether, phthaline, phthalimide and $R_2$ represents an alkyl group with 1–8 carbon atoms the alkyl group being ethyl, propyl, butyl, hexyl, isopropyl, iso-butyl, tert-butyl, cyclohexyl which comprises reacting bisphenols of the formula

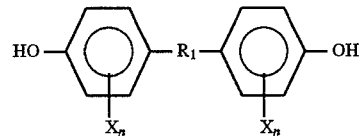

where $R_1$ represents ispropylidene, hexafluoroisopropylidene, cyclohexane, sulphone, ketone, ether, phthaline, phthalimide with dialkylcarbonates in presence of a catalyst selected from organometallic compounds of tin and titanium under inert atmosphere at a temperature in the range of 80°–150°C.

12 Claims, 1 Drawing Sheet

PROCESS FOR THE PREPARATION OF MONO-ALKYLCARBONATE OF BISPHENOLS

This invention relates to a process for the synthesis of Monoalkylcarbonates of bisphenols.

Mono- and bis-alkylcarbonates of bisphenols are useful monomers for the synthesis of a variety of high performance polymers. Bisphenol-A bismethylcarbonate has been melt polymerized with dimethylesters of phthalic acid to form high molecular weight poly(arylester)s. [C. Berti et al, Macromolecules, 24,5269 (1991)]. Bisphenol-A bismethylcarbonate can be self polymerized in a melt in the presence of a catalyst to give high molecular weight poly (arylcarbonate)s. [Japan patent 01,04,617 (1989), Japan patent 63.223,035 (1988)].

In our copending Indian patent application No. 1239/Del/89, We have described and claimed a process for the synthesis of a variety of poly(ester-carbonate)s where use of mono-alkylcarbonate of bisphenol is made.

Bis-alkylcarbonates of bisphenol-A have been previously prepared by the reaction of bisphenol bis(chloroformate) with alcohol in the presence of pyridine as an acid acceptor [H. Schnell and L. Bottenbruch, Macromol. chem. 57,1 (1962)]. This procedure has the drawback of the need to use phosgene to prepare the bisphenol-A bischloroformate, Phosgene is a toxic and hazardous chemical whose handling in industrial practice is increasingly becoming difficult. Additionally, the process produces pyridine hydrochloride salt as byproduct whose disposal requires further treatment with alkali.

The synthesis of mono- and bis-alkylcarbonates in the prior art involves reaction of aromatic dihydroxy compounds with alkylaryl carbonate.

Alkylarylcarbonate has to be obtained by chloroformate approach or- with dialkylcarbonate using a suitable catalysts.

This method is beset with following disadvantages.

1) Chloroformate route involves the use of phosgene.

2) It is very difficult to obtain alkylarylcarbonate in pure form by carbonate interchange reaction between aromatic monohydroxy compound and dialkylcarbonate because this reaction yields mainly diarylcarbonate. Moreover, this reaction is thermodynamically unfavorable.

3) The reaction of an aromatic dihydroxy compound and alkylarylcarbonate yields mono and bis-alkylcarbonate only after the removal of high boiling point phenol which requires relatively higher temperature. Due to higher temperature, it is difficult to obtain mono- and bis-alkyl carbonate of aromatic dihydroxy compounds in a pure form. [Japan Patent 01,47,740 (1989)].

The synthesis of mono-alkylcarbonates of bisphenols has not been disclosed in the prior art by carbonate interchange reaction with dialkylcarbonates.

The main object of the present invention is to provide an improved process for the preparation of mono-alkylcarbonate of hisphenols without the use of phosgene.

Figure 1:
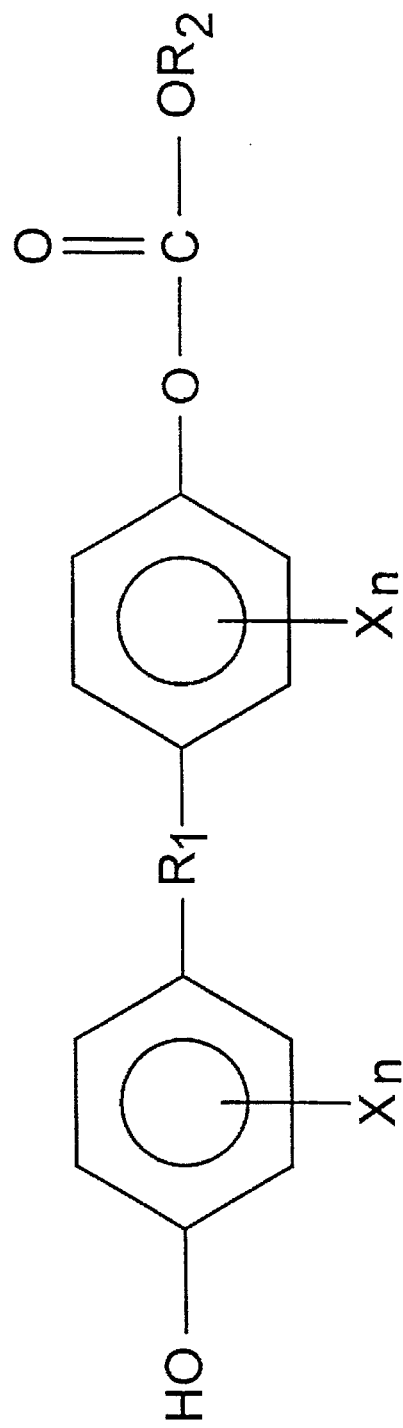
FIG. 1 shows the formula of a bisphenol monoalkyl carbonate produced by the process of this invention.
Figure 2:
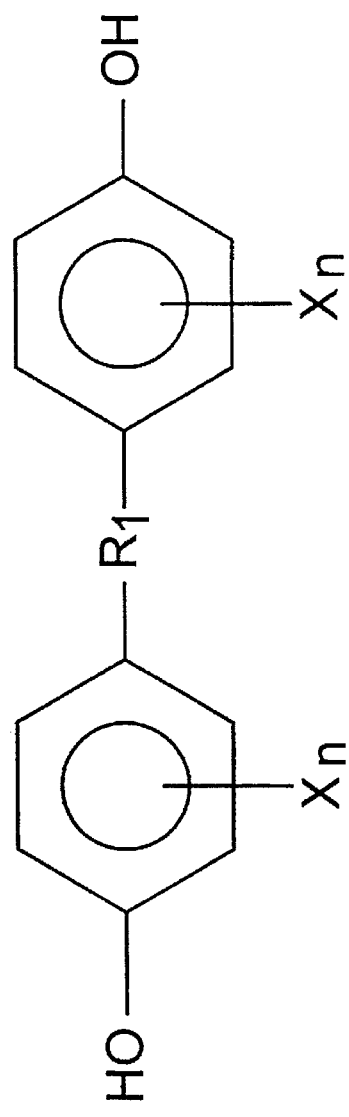
FIG.2 shows the formula of a bisphenol used as starting material.

Accordingly, the present invention provides an improved process for the preparation of mono-alkylcarbonate of bisphenols of the formula I shown in FIG. 1 of the drawing accompanying this specification where $R_1$ represents ispropylidene, hexa-fluoroisopropylidene, cyclohexane, sulphone, ketone, ether, phthaline, phthalimide and $R_2$ represents an alkyl group with 1–8 carbon atoms the alkyl group being ethyl, propyl, butyl, hexyl, isopropyl, isobutyl, tert-butyl, cyclohexyl which comprises reacting bisphenols of the formula II shown in FIG. 2 where $R_1$ represents ispropylidene, hexafluoroisopropylidene, cyclohexane, sulphone, ketone, ether, phthaline and phthalimide with dialkylcarbonates in presence of a catalyst selected from organometallic compounds of tin and titanium under inert atmosphere at a temperature in the range of 80°–150° C.

The reaction can be carried out in an apparatus comprising a round bottom three neck flask supporting to a one to one and half foot fractionating column provided with a liquid dividing head. The bisphenols and catalyst are first reacted followed by addition of dialkylcarbonate or all the reagents are introduced at once into the reaction flask. The reaction may be carried out in liquid phase preferably using 2 to 30 fold excess of dialkylcarbonate, in the absence of solvent, preferably at a lower temperature in the range of 90°–120° C. Low boiling alcohol is distilled off slowly as an azeotrope with dialkylcarbonate. The inert atmosphere is maintained by the use inert gas nitrogen and the reaction may be effected for a period ranging from 6–24 hours. The final temperature of the reaction mixture is critical in obtaining high yields of the mono-alkylcarbonate of bisphenols. Higher temperature causes reduction in the yield of the desired compounds with concomitant formation of oligomers. After the desired period of reaction excess of dialkylcarbonate is removed under vacuum (0.1 mm Hg) at a temperature of 25°–40° C. Thereafter, the product mixture is analyzed by thin layer chromatography which shows formation of desired product and unreacted bisphenols. The pure compound, namely mono-alkylcarbonate of bisphenols can be separated by column chromatography over an adsorbent bed of silica gel (60–120 mesh) using a suitable solvent mixture.

The dialkylcarbonate suitable for the process can be chosen from dimethyl carbonate, diethyl carbonate, di-n-butyl, di-tert.butyl, diamyl, diheptyl, dihexyl and dicyclopropyl carbonate. However, the desirable dialkyl carbonate is dimethyl carbonate because while forming the carbonate bond the methyl group separates out as methanol because of lower boiling point.

The $R_1$ group in bisphenol in formula I can be selected from the following: isopropylidene, methylene, methylmethylene, ethylmethylene, isobutylmethylmethylene, diphenylmethylene, phenylmethylmethylene, hexa-fluoroisopropylidene, phthaleines,phthalimides, N-substituted phthalimides (methyl,phenyl ), 1,4-phenylene, 1,4-naphthalene, dihydroanthracene, spirobisindanes, indanes, thiophenes, azo, dimethylsilane, diphenylsilane, siloxane, hydroquinoids, cyclopentane, cyclohexane, ether, sulfide, sulfoxide, sulphone, ketone, ester and amide. The bisphenols used may have substituents on aromatic ring which consist of a straight chain of 1 to 4 carbon atoms or alkyl group consisting of branching or a phenyl group or a halogen atom and n is an integer from 1 to 4. The $R_2$ in mono-alkylcarbonate of hisphenol in formula II can be an alkyl group with 1–8 carbon atoms, the alkyl group being ethyl, propyl, butyl, hexyl, isopropyl, iso-butyl, tert-butyl or cyclohexyl.

The amount of catalyst employed ranges from $10^{-2}$ to $10^{-6}$ mole per mole of bisphenol, the preferred amount being $10^{-2}$ to $10^{-4}$ mole per mole of bisphenol The catalyst can be chosen from amongst the wide variety of metal organic compounds known. Examples are di-n-butyltin oxide, di-n-butyltin diacetate, tri-n-butyltin hydroxide, n-butyltin tributoxide, n-tetratyltin, di-n-butyltin dimethoxide, tinoxalate, di-n-butyltin dilaurate, tri-n-butyltin halide (Cl,Br), di-n-butyltin dihalide (Cl, Br) and stannoxanes having general formula ($XR_1R_2Sn)_2O$ where $R_1,R_2$=alkyl,aryl,substituted aryl (Cl, Br,$NO_2$,—$OCH_3$, —$CH_3$, —CN) ( o, m, p), X=O-aryl, 0-alkyl, acetate, phenate, halogens (Cl, Br). Titanium compounds such as titanium isoproxide, titanium butoxide, titanium aryloxide can also be employed. In case of titanium aryloxide,the aryl group may have a substitutent [Cl,Br,$NO_2$,$CH_3$, $OCH_3$(o, m or p)] or be unsubstituted.

The main advantages of the invention are that, unlike the hitherto known processes, the present invention uses dialkylcarbonate, a safe, and clean substitute for phosgene. No organic solvents are used in the reaction. The reaction byproduct is methanol, which can easily be recycled or reused elsewhere.

The invention is illustrated by the examples given below which should not be construed to limit the scope of the invention

EXAMPLE - I 5.7 g of bisphenol-A was reacted with 0.167 g of tetrabutyl 3 diphenoxystannoxane at 150° C. 21.4 g of dimethylcarbonate (DMC) was added dropwise over a period of half an hour. The reaction temperature decreased to 94° C. A total distillate of 6 mL consisting of byproduct methanol and DMC was obtained in 24 hours. Reaction temperature was gradually increased to 102° C. and held for 3 hours. Excess of DMC was removed under vacuum (0.1 mm Hg) at 30° C. Reaction product was analyzed by thin layer chromatography (TLC). Mixture of products obtained were separated by column chromatography using petroleumether-chloroform eluent mixture. Monomethylcarbonate of bisphenol-A 3.3 g was isolated with a total conversion of 72%

EXAMPLE - II

The reaction between 1.5 cyclohexane and 9.9 g of DMC was carried out in the presence of 0.037 g of tetrabutyl-1,3 diphenoxystannoxane catalyst. The reaction temperature was 95° C. and 2 mL of distillate consisting of byproduct methanol and DMC was distilled in 24 hours reaction time. The pot temperature increased to 102° C. Excess DMC was removed under vacuum (0.1 mm Hg) at 30° C. and reaction product was analyzed by TLC. Mixture of products obtained were separated by column chromatography using petroleumether-benzene solvent mixture as eluent. Monomethylcarbonate of 1,1-bis (4-hyroxy phenyl)cyclohexane 0.84 g (46% ) yield with a total conversion of 55.5% was obtained.

EXAMPLE - III

A mixture of 2,2 bis (4 hydroxy 3 methyl phenyl) propane (2 g), DMC (14 g) and tetrabutyl 1,3 diphenoxystannoxane (0.052 g) in a molar ratio of 1:20:0.005 was reacted at 96° C. A distillate of 3.5 mL consisting of byproduct methanol and DMC was distilled in 24 hours reaction time. The pot temperature was increased to 102° C. Excess DMC was removed under vacuum (0.1 mm Hg) at 30° C. and product analyzed by TLC. Reaction product mixture was separated by column chromatography using Petroleum ether-benzene solvent mixture. Monomethylcarbonate of 2,2-bis(4-hydroxy-3-methylphenyl)propane 0.84 g (34%) yield with a total conversion of 36% was obtained.

EXAMPLE - IV

A reaction of hydroquinone (11 g), DMC (32 g) and di-n-butyltinoxide(0.025 g) as catalyst in a molar ratio of 1:3.5:0.01 was carried out at 95° C. A distillate of 9.5 mL consisting of byproduct methanol and DMC was distilled in 24 hours reaction time. The pot temperature was increased to 105° C. Excess DMC was removed under vacuum (0.1 mm Hg) at 30° C. and reaction product analyzed by TLC. Product mixture obtained were separated by column chromatography using benzene-ethylacetate mixture as eluent p-hydroxyphenylmethylcarbonate 4.58 g (27%) yield with a total conversion of 32% was obtained

EXAMPLE - V

A mixture of 4,4-biphenol (2g), DMC (30 g) and tetrabutyl 1,3-diphenoxystannoxane (0.071 g) in a molar ratio of 1:30:0.005 was reacted at 93° C. A distillate of 3.5 mL consisting of byproduct methanol and DMC was distilled in 24 hours reaction time and pot temperature was gradually increased to 96° C. Excess DMC was removed under (0.1 mm Hg) vacuum at 30° C. Reaction product was analyzed by TLC and product separated by column chromatography using petroleumether-acetone solvent mixture as eluent. Monomethylcarbonate of 4,4-biphenol 0.6 g (23%) yield with a total conversion of 27% was obtained.

EXAMPLE - VI 2 g of 4,4-(hexa-fluoroisopropylidene)diphenol was reacted with 0.039 g of tetrabutyl-13-diphenoxystannoxane catalyst at 160° C. 5.35 g of DMC was added dropwise over a period of half an hour. The reaction temperature decreased to 94° C. A total distillate of 1.2 mL consisting of byproduct methanol and DMC was obtained in 24 hours reaction time The reaction temperature was increased to 100° C. Excess DMC was removed under vacuum (0.1 mm Hg) at 30° C. Reaction product was analyzed by TLC and separated by column chromatography using petroleumether- acetone as eluent mixture. Monomethyl carbonate of 4,4-(hexafluoroisopropylidene) diphenol 0.37 g (17%) yield with a total conversion to 17% was obtained.

EXAMPLE - VII

The reaction of 4,4-sulfonyldiphenol (2 g) and DMC (21.4 g) was carried out in presence of tetrabutyl-1,3-diphenoxystannoxane (0.053 g) in a molar ratio of 1:30:0.005. The reaction temperature was 92° C. 3.6 mL of distillate consisting of by product methanol and DMC was distilled in 24 hours reaction time. The pot temperature was increased to 95° C. Excess DMC was removed under vacuum (0.1 mm Hg) at 30° C. and reaction product was analyzed by TLC. Product obtained was separated by column chromatography using petroleumether- acetone mixture as eluent. Monomethyl carbonate of 4,4-sulfonyldiphenol 0.08 g (3.20%) yield with a total conversion to 3.25% was obtained.

We claim:

1. A process for the preparation of mono-alkylcarbonate of bisphenols of formula I

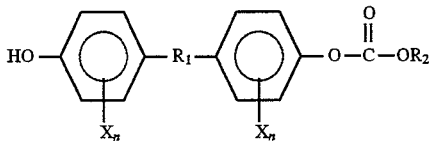

where $R_1$ represents an ispropylidene, hexafluoroispropylidene, cyclohexane, sulphone, keto, ether, phthaline or phthalimide group, $R_2$ represents an alkyl group with 1–8 carbon atoms, X is selected from straight or branched, chain alkyl groups of 1 to 4 carbon atoms, a phenyl group and halogen atoms and n is from 1 to 4 which comprises reacting a bisphenol of the formula II

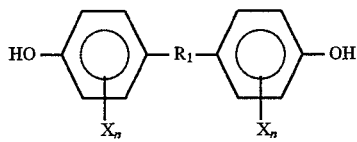

where $R_1$ represents an ispropylidene, hexafluoroispropylidene, cyclohexane, sulphone, keto or phthalimide group, X is selected from straight or branched chain alkyl groups of 1 to 4 carbon atoms, a phenyl group and halogen atoms and n is from 1 to 4 with a dialkylcarbonate in the presence of a catalyst selected from organo-metallic compounds from the group consisting of di-n-butyltin oxide, di-n-butyltin diacetate, tri-n-butyltin hydroxide n-butyltin tributoxide, di-n-butyltin dimethoxide, tin oxalate, di-n-butyltin dilaurate, tri-n-butyltin halides, stannoxanes, titanium isopropoxide, titanium butoxide, and titanium aryl oxides, under inert atmosphere at a temperature in the range 60°–150° C.

2. A process as claimed in claim 1 wherein the dialkylcarbonate is selected from dimethylcarbonate, diethylcarbonate, di-n-butylcarbonate, di-tert.-butylcarbonate, diamylcarbonate, diheptylcarbonate, dicyclohexylcarbonate and dicyclopropylcarbonate.

3. A process as claimed in claim 1 wherein the dialkylcarbonate is used in 2–30 fold excess over the bisphenol.

4. A process as claimed in claim 1 wherein the catalyst used is selected from di-n-butyltinoxide, di-n-butyltin dilaurate, di-n-butyltin dimethoxide, di-n-butyltin diacetate, tri-n-butyltin hydroxide, tetrabutyl-1, 3-diphenoxystannoxane, titanium isopropoxide, titanium-n-butoxide and titanium tetraphenoxide.

5. A process as claimed in claim 1 wherein the reaction of bisphenol with dialkylcarbonate is conducted in the liquid phase in the absence of a solvent.

6. A process as claimed in claim 1 wherein the reaction of bisphenol with dialkylcarbonate is conducted for 6–24 hours.

7. A process as claimed in claim 1 wherein after the desired reaction period, excess dialkylcarbonate is removed under vacuum (0.1 mm Hg) taking care that the pot temperature does not exceed 40° C.

8. A process as claimed in claim 1 wherein the monoalkylcarbonate of bisphenol formed is separated by column chromatographic techniques.

9. A process according to claim 1 wherein $R^2$ is selected from ethyl, propyl, butyl, hexyl, isopropyl, tert-butyl an cyclohexyl groups.

10. A process according to claim 1 wherein said dialkyl carbonate is dimethyl carbonate.

11. A process according to claim 1 wherein the catalyst is tetrabutyl 1,3 diphenoxystannoxane.

12. A process according to claim 10 wherein said compound of formula II is selected from bisphenol A or 1,1 bis(4-hydroxyphenyl)cyclohexane/and is reacted with dimethyl carbonate.

* * * * *